United States Patent [19]

Reineke

[11] 4,038,245
[45] July 26, 1977

[54] CHAR-FORMING POLYMER COMPOSITIONS

[75] Inventor: Charles E. Reineke, Midland, Mich.

[73] Assignee: The Dow Chemical Company, Midland, Mich.

[21] Appl. No.: 688,862

[22] Filed: May 21, 1976

[51] Int. Cl.² .............................................. C08K 5/41
[52] U.S. Cl. ...................... 260/45.7 S; 260/DIG. 24; 526/3
[58] Field of Search .................. 260/DIG. 24, 456 R, 260/45.7 S; 526/3

[56] References Cited
U.S. PATENT DOCUMENTS 3,346,612  10/1967  Hansen ..................................... 526/3

Primary Examiner—Lewis T. Jacobs

Attorney, Agent, or Firm—James B. Guffey

[57] ABSTRACT

Esters of the formula:

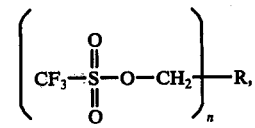

wherein R is an n-valent tertiary hydrocarbyl radical or an inertly substituted n-valent tertiary hydrocarbyl radical, promote char formation in polymer compositions containing a monovinylidene aromatic monomer, such as styrene, and an ethylenically unsaturated carboxylic anhydride, such as maleic anhydride.

10 Claims, No Drawings

CHAR-FORMING POLYMER COMPOSITIONS

BACKGROUND OF THE INVENTION

This invention relates to char-forming aromatic polymer compositions containing ester of trifluoromethanesulfonic acid.

Polymer compositions having reduced propensity to burn have generally been prepared by incorporating therein halogenated materials. Such materials are thought to operate to inhibit combustion in the gaseous phase adjacent to the polymer surface by the release of halogen-containing vapors at elevated temperatures. See for example, U.S. Pat. Nos. 3,700,957; 3,773,825; 3,775,367; and 3,804,885. Such halogenated materials are hereinafter also referred to as conventional combustion inhibitors. However, these halogenated materials often have a plasticizing effect on the polymer composition, particularly at the elevated temperatures accompanying a fire. Therefore the presence of such materials often deleteriously affects the structural integrity of polymeric articles under such conditions and can significantly increase the dripping of molten polymer.

The effectiveness of halogenated combustion-inhibiting agents can be enhanced by the formation of a rigid char barrier that prevents or at least impedes the migration of combustible fuel to the point of combustion. Such a char barrier serves to enhance the structural integrity of the burning polymeric article, to inhibit dripping of molten polymer and to thermally insulate the unburned portion from the heat generated by combustion. The formation of char also often reduces the smoke emission of burning polymer compositions. U.S. Pat. No. 3,810,862 describes char-forming, flame-retardant polyolefin compositions.

In view of the advantages of char formation upon combustion of polymer compositions and in view of the general unavailability of char-forming aromatic polymer compositions, it would be highly desirable to provide such char-forming polymer compositions.

SUMMARY OF THE INVENTION

This invention is a char-forming composition of matter comprising (A) a polymeric component that comprises (1) polymerized ethylenically unsaturated carboxylic ahydride in an amount sufficient to provide at least about 1 milliequivalent of anhydride moiety per gram of the char-forming composition, and (2) polymerized monovinylidene aromatic monomer in an amount sufficient to provide at least about 1 milliequivalent of reactive aromatic moiety per gram of the char-forming composition, and (B) a char-forming amount of a stable ester of the formula:

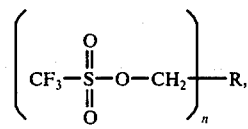

wherein n is a positive integer and R is an n-valent tertiary hydrocarbyl radical or an inertly substituted n-valent tertiary hydrocarbyl radical.

Such compositions are useful in the manufacture of molded articles such as containers, housings for machines and electrical equipment, cabinets for electrical appliances, and the like. Such compositions are also useful in foamed form in applications such as thermal insulation, light construction, furniture manufacture, and the like.

DETAILED DESCRIPTION OF THE INVENTION

The polymeric component of the present invention is a normally solid thermoplastic material. Such component can be a single copolymer or a blend of two or more polymers or copolymers.

In the polymeric component, it is understood that the anhydride moiety and the aromatic moiety are integral parts of the same or different polymer molecules. Thus the anhydride moiety and the reactive aromatic moiety may be incorporated into a single copolymer or each may be incorporated into different polymer or copolymer ingredients of a polymeric blend. Preferably the anhydride moiety and the reactive aromatic moiety are contained within a single copolymer within such polymeric component.

As used herein polymerized ethylenically unsaturated carboxylic anhydride means an ethylenically unsaturated carboxylic anhydride (a) which has undergone addition polymerization with itself or with another ethylenically unsaturated monomer to form a normally solid thermoplastic polymer or copolymer, and (b) which contains at least one anhydride moiety of the formula

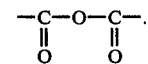

Most common of such carboxylic anhydrides, and therefore of particular interest in the practice of this invention, are the α,β-ethylenically unsaturated carboxylic anhydrides. Exemplary α,β-ethylenically unsaturated carboxylic anhydrides include maleic anhydride, phenylmaleic anhydride, citraconic anhydride, itaconic anhydride, chloromaleic anhydride, bromomaleic anhydride, and the like. The anhydride is preferably maleic anhydride, chloromaleic anhydride or bromomaleic anhydride, and is most preferably maleic anhydride.

As used herein polymerized monovinylidene aromatic monomer means a monomer (a) which has undergone addition polymerization with itself or with another ethylenically unsaturated monomer to form a normally solid thermoplastic polymer or copolymer, and (b) which contains at least one reactive hydrocarbon aromatic moiety of the formula:

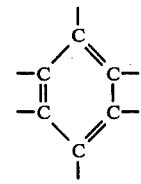

to which is attached, prior to polymerization, a radical of the formula:

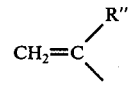

wherein R" is hydrogen or lower alkyl having from 1 to about 4 carbon atoms such as methyl, ethyl, propyl and butyl. By a reactive aromatic moiety is meant that it has one or more ring positions available for substitution, advantageously electrophilic aromatic substitution.

Preferably the monovinylidene aromatic monomer is a compound of the formula:

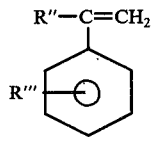

wherein R" is as previously defined and R''' is hydrogen, bromine, chlorine, an alkyl radical of from 1 to about 6 carbon atoms or a haloalkyl radical having from 1 to about 6 carbon atoms and from 1 to about 3 atoms of bromine or chlorine. Examples of such preferred species are styrene, α-methylstyrene, ar-methylstyrene, ar-(t-butyl)styrene, ar-chlorostyrene, ar-bromostyrene, ar-(chloromethyl)styrene, and the like.

Most preferably the monovinylidene aromatic monomer is styrene.

In addition to the aforementioned polymerized monomers, the polymeric component may contain other polymerized ethylenically unsaturated monomers. Such other monomers may be present in the form of a copolymer with the carboxylic anhydride, the aromatic monomer, or both; in the form of a homopolymer of such other monomer; or in the form of a copolymer of such other monomers among themselves. Examples of such other monomers are α,β-ethylenically unsaturated nitriles such as acrylonitrile, methacrylonitrile; alkyl esters of α,β-ethylenically unsaturated carboxylic acids, e.g., ethyl acrylate, butyl acrylate and methyl methacrylate; vinyl esters, e.g., vinyl acetate; α-olefins, e.g., ethylene, propylene and butene-1; conjugated dienes, e.g., butadiene and isoprene and similar ethylenically unsaturated monomers.

The exact ratios of the chosen monomers may vary, as required for a particular application based upon physical property considerations so long as the aforementioned required concentrations of aromatic moiety and anhydride moiety are present. However, as a general rule, the polymeric component will preferably contain (1) the polymerized ethylenically unsaturated carboxylic anhydride in an amount sufficient to provide from about 2 to about 5, especially from about 2.5 to about 4, milliequivalents of anhydride moiety per gram of the char-forming composition, and (2) the polymerized monovinylidene aromatic monomer in an amount sufficient to provide from about 2 to about 8, especially from about 4 to about 7.5, milliequivalents of reactive moiety per gram of the char-forming composition.

Of particular interest as polymeric components are the monovinylidene aromatic/ethylenically unsaturated anhydride copolymers, especially the styrene/maleic anhydride copolymers, containing from about 50 to about 80, preferably from about 60 to about 75, mole percent of aromatic monomer and from about 20 to about 50, preferably from about 25 to about 40, mole percent of anhydride monomer.

Methods for preparing the aforementioned polymeric components are those commonly employed in preparing conventional addition polymers.

The trifluoromethanesulfonates used in the practice of this invention, hereinafter sometimes referred to as triflate esters, are stable esters of the formula:

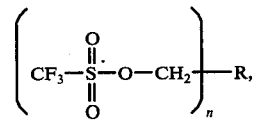

wherein n and R are as defined hereinbefore.

The term "stable" as used herein connotes both thermal stability and low volatility. For the purpose of this invention, a triflate ester is deemed stable (a) if it is as thermally stable as 2,2-dimethyl-propyl trifluoromethanesulfonate, preferably as stable as 3-bromo-2,2-bis(-bromomethyl)-propyl trifluoromethanesulfonate, and (b) if it has a boiling point of at least about 60° C, preferably at least about 100° C, at a pressure of about 3 millimeters of mercury.

The triflate esters comprise a number of triflate ester moieties of the formula, $CF_3-SO_3-CH_2-$, corresponding to n wherein is a positive integer. Preferably n is from 1 to about 9; more preferably n is from 1 to about 6; and most preferably n is 1 or 2.

In the triflate esters, R is an n-valent tertiary hydrocarbyl radical, or an inertly substituted n-valent tertiary hydrocarbyl radical. Preferably such radical contains from 1 to about 9 valency carbon atoms, more preferably from 1 to about 3 valency carbon atoms, and most preferably 1 valency carbon atom. As used herein, valency carbon atom means the carbon atom, within the radical R, which is bonded to one or more triflate ester moieties, as previously defined.

As used herein, n-valent means that the hydrocarbyl radical is bonded to n triflate ester moieties.

The term "tertiary" means that each valency carbon atom in the hydrocarbyl radical is bonded to 4 carbon atom including the carbon atom in each triflate ester moiety to which the valency carbon atom is bonded. Accordingly, the valency carbon atom will be bonded to between zero and 3 carbon atoms which are not contained within a triflate ester moiety. Thus the hydrocarbyl radical is "tertiary" in the sense that, as to a given triflate ester moiety, it is tertiary (i.e., bonded to 3 additional carbon atoms).

Subject to the requirement that each valency carbon atom is bonded to a total of 4 carbon atoms, the tertiary hydrocarbyl radical can be an aliphatic, alicyclic or aromatic radical, for example, an alkyl radical, an alkenyl radical, a cycloalkyl radical, a cycloalkenyl radical, an aralkyl radical, an aralkenyl radical, an arcycloalkyl radical, an arcycloalkenyl radical, and the like.

The term "inertly substituted" means that the hydrocarbyl radical contains substituents, such as halogen atoms, and chain linkages, such as oxygen or sulfur atoms, which do not interfere with the preparation of the triflate ester. Thus, for example, inertly substituted tertiary hydrocarbyl radicals include halogenated tertiary hydrocarbyl radicals such as halo-t-alkyl, haloaryl-t-alkyl and similar halogenated tertiary hydrocarbyls wherein tertiary hydrocarbyl is as defined and exemplified hereinbefore; hydrocarbyloxy-t-hydrocarbyl radicals such as, alkoxy-t-alkyl, haloaryloxy-t-alkyl, aryloxy-t-alkenyl and similar radicals wherein tertiary hydrocarbyl is as defined hereinbefore and hydrocarbyl is alkyl, haloalkyl, aryl, haloaryl, aralkyl, alkenyl, aralkenyl, cycloalkyl, cycloalkenyl, arcycloalkyl, arcycloalkenyl, alkaryl, alkenylaryl, cycloalkylaryl, cycloalkenylaryl and similar monovalent hydrocarbyl and halogenated hydrocarbyl radicals; and hydrocarbylthio-t-hydrocarbyl radicals, such as alkylthio-t-alkyl, haloarylthio-t-alkyl, cycloalkylthio-t-alkyl, alkarylthio-t-cycloalkenyl, and similar hydrocarbyl and halogenated hydrocarbyl radicals wherein tertiary hydrocarbyl and hydrocarbyl are as defined and exemplified hereinbefore.

While the total carbon content of the radical R is not critical, it will generally contain from 1 to about 40, preferably from 1 to about 24, and most preferably from 1 to about 18 carbon atoms.

Naturally since R is "tertiary" as to a single triflate ester moiety, the minimum possible carbon content of R will depend upon the number of triflate ester moieties to which R is bonded and upon the number of valency carbon atoms contained by R. Thus, for example, when R contains one valency carbon atom, the minimum carbon content of R is (5-n) wherein valency carbon atom and n are as hereinbefore defined. Similarly when R contains 2 valency carbon atoms, the minimum carbon content of R is (8-n). In a like manner when R contains more than 2 valency carbon atoms, the minimum carbon content of R will be that which is required, for a given value of n, for each valency carbon to be bonded to a total of 4 carbon atoms.

Of particular interest in the practice of this invention are the triflate esters wherein R is an inertly substituted hydrocarbyl radical containing one or more halogen atoms selected from the group consisting of bromine or chlorine. Those esters wherein such halogen is bromine are especially preferred. Preferably the halogen content of the inertly substituted radical is such that the ratio of halogen atoms to carbon atoms in R is from about 1:10 to about 1:1, most preferably from about 1:2 to about 1:1.

In an especially preferred embodiment of the invention, the triflate ester of the char-forming composition has the formula

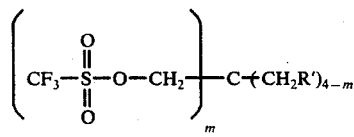

wherein $m$ is 1 or 2 and each R' group is independently bromine or an inertly substituted aliphatic, alicyclic or aromatic halohydrocarbon radical containing from 1 to about 6 carbon atoms and from 1 to about 4 atoms of bromine. Preferably such R' group is independently bromine or tribromophenoxy.

The triflate esters used in the practice of this invention can be conveniently prepared by contacting trifluoromethanesulfonic anhydride with a cooled (e.g., 0° C), stirred solution containing an inert organic solvent such as methylene chloride, an acid acceptor such as pyridine, and a hydroxy-containing compound of the formula:

wherein n and R are as previously defined. The procedure for preparing esters of para-toluenesulfonic acid described by Fieser et al., "Reagents for Organic Synthesis," John Wiley & Sons, Inc., New York, N.Y., 1967, p. 1180 can be conveniently employed in the preparation of such triflate esters.

The aforementioned triflate esters are present in the char-forming compositions of the invention in a char-forming amount. As used herein, the phrase "char-forming composition" means a composition characterized by formation of char upon combustion. The term "char-forming amount" means that amount required to cause the composition to form char, as hereinafter defined, upon combustion.

By the term "char" is meant a black, dry solid which appears upon the surface of a molded article upon combustion and before cooling. Such solid is distinct and readily separable from the underlying polymer after cooling and is visually observable without the aid of magnification for a person having normal (i.e., 20:20) vision. the amount of char formed is measured quantitatively by comparing the residual weight of polymeric component samples, with and without the triflate esters, after each sample has been exposed to elevated temperatures. Such measurement technique is often called thermogravimetric analysis.

The maximum amount of char formation attainable for a given composition of the invention is dependent upon the amounts of the critical moieties (i.e., the reactive aromatic moiety and the anhydride moiety) present in the polymeric component. For any particular polymeric component, the amount of char formation relative to the maximum achievable for such composition is dependent upon the triflate ester content of the composition. Thus, although it is necessary that only a char-forming amount of the triflate ester be used, a larger amount of the triflate ester may be advantageously used to achieve the maximum char-forming potential of the chosen polymeric component.

As a general rule, however, the triflate ester is beneficially present in an amount sufficient to provide from about 0.1 to about 1, preferably from about 0.1 to about 0.6, most preferably from about 0.1 to about 0.4, milliequivalent of triflate ester moiety

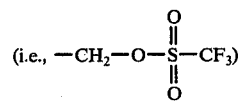

per gram of char-forming composition.

The char-forming compositions of this invention optionally contain a small but effective amount of a halogenated organic compound for conventional combustion inhibition. Any such compound which is compatible with the polymer component may be employed. Examples of such compounds are (a) organic compounds which contain from about 25 to about 90 weight percent chlorine and which have either α-hydrogen and/or α-chlorine available for dehydrochlorination or dechlorination, such as chlorinated paraffins, chlorinated polyethylene, chlorinated castor oil, chlorinated tall oil, chlorinated cyclic hydrocarbons (e.g., hexachlorocyclohexane, hexachlorododecane, etc.), chlorinated acyclic hydrocarbons (e.g., hexachloroethane, pentachloroethane, hexachloropropane, etc.), and the like; (b) organic compounds which contain from about 30 to about 95 weight percent bromine and which have either α-hydrogen or α-halogen available for dehydrobromination or dehalogenation, such as hexabromocyclohexane, lower brominated cyclohexanes, octabromododecane, 1,2,3,4-tetrabromobutane, 1,2- dibromoethylbenzene, hexabromoethane, acetylene tetrabromide, hexabromocyclododecane, octabromohexadecane, and the like; (c) brominated organic compounds having bromine atoms(s) substituted on aromatic or vinyl carbon atoms or otherwise situated so that no α-hydrogen or α-halogen is available for normal dehydrohalogenation or dehalogenation, such as hexabromobenzene, pentabromobenzene, decabromobiphenyl, pentabromodiphenyl ether, tribromoneopentyl alcohol and esters thereof, bis(2,3-dibromo-2-butenediol) ester of tris(bromomethyl)acetic acid, and the like; and (d) counterparts of such exemplified organic compounds wherein such counterpart contains both bromine and chlorine rather than bromine or chlorine alone.

Such halogenated organic compounds, if used, will generally be present in an amount of from about 2 to about 25, preferably from about 5 to about 15 percent by weight based upon the total weight of the char-forming composition.

In fact the compositions of this invention containing bromine, chlorine or both, whether in conjunction with an additive as above described, as an integral part of the polymeric component or as inert substituents of the triflate ester, are of particular interest in the practice of this invention since such compositions exhibit conventional combustion inhibition in combination with char-forming characteristics.

Further, the compositions of the invention optionally contain other additives such as pigments, thermal stabilizers, U.V. stabilizers, antistatic agents, etc. Care should be exercised in the use of such other additives that the additives chosen and the amounts used do not deleteriously affect the char-forming characteristics of the composition of the invention.

The triflate esters as well as the aforementioned optional additives can be incorporated into the polymeric component to form the composition of the invention by any of the usual methods, such as extrusion compounding, roll or ball milling, solution blending and the like.

The resulting char-forming compositions are readily fabricated into desired useful articles by conventional fabrication means such as injection molding, extrusion and the like.

The practice of the invention is further illustrated by the following examples.

EXAMPLE 1

Preparation of Additive A:
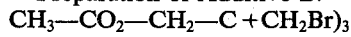
$CF_3—SO_3—CH_2—C{+CH_2Br)_3}$

A solution of 25.5 grams (0.09 mole) of trifluoromethanesulfonic anhydride in methylene chloride is added dropwise, with stirring, over a one and a half hour period to a solution containing 26.0 grams (0.08 mole) of 3-bromo-2,2-bis(bromomethyl)-1-propanol and 6.3 grams (0.08 mole) pyridine in 75 ml of methylene chloride, at 0° C.

The reaction product is recovered by:
1. washing the reaction mixture with 100 ml of cold distilled water in a separatory funnel and draining off the methylene chloride solution layer;
2. drying the methylene chloride layer over anhydrous sodium sulfate;
3. filtering out the sodium sulfate; and
4. vacuum distillation of the methylene chloride.

The product recovered is a colorless liquid exhibiting a boiling point of 102° C at 0.03 mm of mercury and a nuclear magnetic resonance (NMR) spectrum in agreement with that expected for 3-bromo-2,2-bis(bromomethyl)-propyl trifluoromethanesulfonate. A 33.5-gram portion of the product is recovered, representing a yield of 91.5 percent.

Preparation of Additive B:
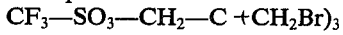
$CH_3—CO_2—CH_2—C{+CH_2Br)_3}$

For comparative purposes a quantity of 3-bromo-2,2-bis(bromomethyl)-propyl acetate is prepared by reacting the 3-bromo-2,2-bis(bromomethyl)-1-propanol with acetic acid.

PREPARATION OF CHAR-FORMING COMPOSITIONS

Polystyrene compositions and styrene/maleic anhydride copolymer compositions, comprising 75 mole percent styrene and 25 mole percent maleic anhydride, each containing the aforementioned triflate ester are prepared by blending the ester into the polystyrene, or the styrene/maleic anhydride copolymer, with a Brabender® mixer at 180° C or 220° C, respectively. In the same manner, compositions containing the aforementioned acetate and polystyrene, or the styrene/maleic anhydride copolymer, are prepared. The resulting compositions are molded into test bars and subjected to a modified version of the Underwriters Laboratory Vertical Burning Test for Classifying Materials 94V-0, 94V-1, or 94V-2. Such tests demonstrate the ignition properties or burning characteristics of the polymer compositions when exposed to small-scale ignition sources. It should be noted, however, that all known synthetic polymers will burn when subjected to a sufficiently intense heat source. Thus the test results may not reflect the properties of the polymer composition under actual fire conditions. The test procedure and test results are summarized in Table I.

TABLE I

| Sample | Polymer | Additive[1] Type | Wt. % | Wt. % Bromine | Wt. % Halogen | Indicated UL 94 Rating[2] | Avg. Time of Flaming Combustion | Visible Char Formation |
|---|---|---|---|---|---|---|---|---|
| 1* | Styrene/maleic anhydride copolymer (75:25) | None | — | — | — | Sustained Combustion | — | — |
| 2 | " | A | 5 | 2.6 | 3.3 | 94V-2 | 5 sec. | Yes |
| 3* | " | B | 5 | 3.3 | 3.3 | 94V-2 | 11 sec. | No |
| 4 | " | A | 10.3 | 5.4 | 6.7 | 94V-0 | <1 sec. | Yes |
| 5* | " | B | 10.3 | 6.7 | 6.7 | 94V-0 | 6 sec. | No |
| 6* | Polystyrene | A | 10.3 | 5.4 | 6.7 | 94V-2 | 3 sec. | No |
| 7* | " | B | 10.3 | 6.7 | 6.7 | 94V-2 | 10 sec. | No |

*Samples 1, 3, 5, 6 and 7 are not embodiments of the invention.
[1]A: 3-bromo-2,2-bis(bromomethyl)-propyl trifluoromethanesulfonate
B: 3-bromo-2,2-bis(bromomethyl)-propyl acetate
[2]Test specimens, 5.0 inches in length by 0.50 inch in width with a maximum thickness of 0.50 inch, are ignited in a draft-free environment while supported vertically lengthwise by a holding clamp attached to the upper ¼ of the specimen with the lower end 12 inches above

TABLE I-continued

| Sample | Polymer | Additive[1] Type | Wt. % | Wt. % Bromine | Wt. % Halogen | Indicated UL 94 Rating[2] | Avg. Time of Flaming Combustion | Visible Char Formation |
|---|---|---|---|---|---|---|---|---| a horizontal layer of dry absorbent surgical cotton having a maximum free-standing thickness of ⅛ inch. Ignition is performed using a Bunsen burner adjusted to produce a ¾ inch blue flame. The flame is placed centrally under the lower end of the test specimen for 10 seconds and is then withdrawn. When the flaming of the specimen ceases, the flame is placed immediately under the specimen for 10 more seconds and is again withdrawn. The parameters observed for classificaton are:
a. Duration of flaming following the first flame application.
b. Duration of flaming following the second flame application.
c. Duration of flaming and glowing following the second flame application.
d. Whether or not the specimens burned up to the holding clamp.
e. Whether or not the specimens dripped flaming particles which ignited the surgical cotton.
Results indicative of a 94V-0 rating are achieved by meeting the following criteria:
a. None of the specimens burn with flaming combustion for more than 10 seconds aftereach flame application.
b. The specimens exhibit no more than an average 10 seconds total flaming combustion for the 2 flame applications combined.
c. None of the specmens burn with flaming or glowing combustion up to the holding clamp.
d. None of the specimens drip flaming particles that ignite the cotton below the specimens.
e. None of the specmens exhibit glowing combustion persisting longer than 30 seconds after the second flame removal.
Results indicative of a 94V-2 rating are achieved by meeting the following criteria:
a. None of the specimens burn with flaming combustion for more than 30 seconds after each flame application.
b. The specimens exhibit no more than an average 50 seconds total flaming combustion for the 2 flame applications combined.
c. None of the specimens burn with flaming or glowing combustion to the holding clamp.
d. Only briefly burning flaming drips, some of which ignited the cotton below the specimen are observed.
e. None of the specimens exhibit glowing combustion more than 60 seconds after the second flame removal.

As is apparent from Table I, the samples containing styrene/maleic anhydride copolymer and the triflate esters form char upon combustion while the samples containing styrene/maleic anhydride copolymer and the corresponding acetate ester do not. Neither the acetate nor the triflate ester induce char formation in styrene homopolymer.

It should be noted in comparing the results for triflate- and acetate-containing samples at the same additive loadins that such samples have equivalent halogen content by weight and that the acetate-containing samples have a higher bromine content by weight than the triflate-containing samples. It should further be noted that the samples containing triflate esters consistently exhibited significantly shorter average duration of flaming combustion than did the corresponding acetatecontaining samples and that this phenomemon was observed both for polystyrene and for styrene/maleic anhydride copolymer as the polymer component.

EXAMPLE 2

Preparation of Additive C: $(CF_3-SO_3-CH_2)_2C(CH_2Br)_2$

Pursuant to the procedure for preparing Additive A in Example 1, 200 grams (0.72 mole) of trifluoromethanesulfonic anhydride is reacted with 94.2 grams (0.36 mole) of 2,2-bis(bromomethyl)-1,3-propanediol. The reaction product is recovered by recrystallization from hexane, yielding 137 grams (72 percent yield) of solid product exhibiting a melting point range of 67°-70° C. The NMR spectrum confirms the above identified structure.

Preparation of Additive D:

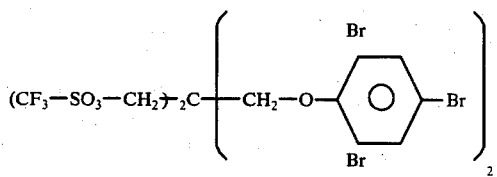

A quantity of 3-bromo-2,2-bis(bromomethyl)-1-propanol is treated with base to form 3,3-bis(bromomethyl)oxetane which is then reacted, with stirring, at room temperature for 30 hours, with a stoichiometric amount of potassium 2,4,6-tribromophenate dissolved in dimethyl formamide. The reaction product formed, 3,3-bis[(2,4,6-tribromophenoxy)methyl]oxetane, is recovered by pouring the reaction mixture into a quantity of distilled water and extracting the resulting mixture twice with methylene chloride. The methylene chloride layers are combined, washed with water, separated from the water wash, and dried over anhydrous sodium sulfate. The sodium sulfate is removed by filtration and the methylene chloride is removed by vacuum distillation on a steam bath. Recrystallization of the resulting crude product from a carbon tetrachloride-hexane mixture provides 3,3-bis[(2,4,6-tribromophenoxy)methyl]oxetane in a 74 percent yield.

The oxetane thus obtained is refluxed for 3 hours in a 15:1 volume ratio mixture of acetic acid and sulfuric acid. The 2,2-bis[(2,4,6-tribromophenoxy)methyl]-1,3-propanediacetate thus formed is recovered by extraction with methylene chloride, which is thereafter removed by vacuum distillation. The resulting diacetate is then refluxed with an excess of methanol in the presence of sodium hydroxide until the NMR spectrum indicates that hydrolysis of the acetate is complete. The resulting product, 2,2-bis[(2,4,6-tribromophenoxy)methyl]-1,3-propanediol, is recovered by (1) removal of the remaining methanol by vacuum distillation, (2) extraction of the product with carbon tetrachloride, (3) drying the CCl$_4$ layer over anhydrous sodium sulfate, and (4) removal of the CCl$_4$ under a vacuum. The 2,2-bis[(2,4,6-tribromophenoxy)methyl]1,3-propanediol thus recovered is then reacted with trifluoromethanesulfonic anhydride according to the following procedure.

A solution of 29.6 grams (0.105 mole) of trifluoromethanesulfonic anhydride in 50 ml of methylene chloride is added dropwise, with stirring, over a 20-minute period to a slurry of 40 grams (0.053 mole) of 2,2-bis[2,4,6-tribromophenoxy)methyl]-1,3-propanediol and 8.3 grams (0.105 mole) or pyridine in 200 ml of methylene chloride. The reaction is allowed to proceed overnight with stirring. The product is recovered in the manner described for Additive A in Example 1, and is further purified by recrystallization from a 2:1 volume ratio mixture of carbon tetrachloride and hexane. The solid product recovered has a melting point range of 142°-145° C. Elemental analysis of the solid product confirms that the solid product is 2,2-bis[2,4,6-tribromophenoxy)methyl]-1,3propanediyl trifluoromethanesulfonate.

Preparation of Additive E:

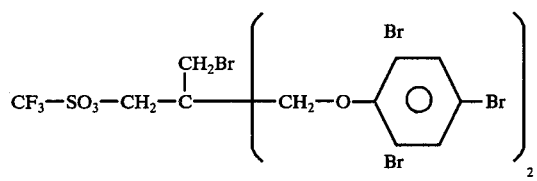

A quantity of 3,3-bis[2,4,6-tribromophenoxy)methyl-]oxetane, produced pursuant to the procedure for Additive D, is reacted in a carbon tetrachloride solution with 62 percent aqueous hydrogen bromide for 30 minutes in a steam bath. The reaction mixture is washed (a) twice with water, (b) once with a dilute sodium bicarbonate solution, and (c) for a third time with water. The carbon tetrachloride layer is separated and dried over anhydrous sodium sulfate. The $CCl_4$ is then removed under a vacuum and the remaining material is further purified by recrystallization of $CCl_4$. The resulting product has a melting point range of 85°–89° C and an NMR spectrum in agreement with that expected for 3-bromo-2,2-bis[(2,4,6-tribromophenoxy)methyl]1-propanol.

The 3-bromo-2,2-bis[(2,4,6-tribromophenoxy)methyl]-1-propanol is then reacted with trifluoromethanesulfonic anhydride pursuant to the procedure for Additive A in Example 1. The resulting product is recovered in 68 percent yield and exhibits a melting point range of 151.5°–153° C. Its NMR spectrum corresponds to that expected for 3-bromo-2,2-bis[(2,4,6-tribromophenoxy)-methyl]-propyl trifluoromethanesulfonate.

PREPARATION AND TESTING OF CHAR-FORMING COMPOSITIONS

Styrene/maleic anhydride copolymer (75:25) compositions containing Additives A, C, D or E are prepared by blending in a Brabender mixer as in Example 1. In the same manner 75:25 styrene/maleic anhydride copolymer compositions containing 3-bromo-2,2-bis(-bromomehtyl)-propyl acetate (i.e., Additive B) are prepared for comparison.

The weight loss of the compositions as a function of temperature is determined by thermogravimetric analysis using a duPont 990 Thermal Analyzer in an air atmosphere at a heating rate of 10° C/minute. The difference between the residual weight of sample containing additive and the residual weight of a sample without additive provides a quantitative measure of the effectiveness of such additive as a char formation promoter in 75:25 styrene/maleic anhydride copolymer. The weights remaining at 450° C for the various compositions and the difference between the residual weights of the samples with and without additive are summarized in Table II.

TABLE II

Thermogravimetric Analysis of 75:25 Styrene/Maleic Anhydride Copolymer Compositions

| Sample | Additive[1] | Wt. % Additive | Residue at 450° C (%)[2,3] | Residue with Additive Minus Residue of Control (i.e., Sample 8) (%)[4] |
|---|---|---|---|---|
| 8* | None | — | 12 | 0 |
| 9* | B | 5 | 15 | 3 |
| 10 | A | 5 | 19 | 7 |
| 11 | C | 5 | 26 | 14 |
| 12* | B | 10 | 10 | −2 |
| 13 | A | 10 | 24 | 12 |
| 14 | C | 10 | 24 | 12 |
| 15 | C | 15 | 27 | 15 |
| 16 | D | 15 | 31 | 19 |
| 17 | E | 15 | 28 | 16 |

*Samples 8, 9 and 12 are not embodiments of the invention.
[1]A: 3-bromo-2,2-bis(bromomethyl)-propyl trifluoromethanesulfonate.
B: 3-bromo-2,2-bis(bromomethyl)-propyl acetate.
C: 2,2-bis(bromomethyl)-1,3-propanediyl trifluoromethanesulfonate.
D: 2,2-bis[(2,4,6-tribromophenoxy)methyl]-1,3-propanediyl trifluoromethanesulfonate.
E: 3-bromo-2,2-bis[(2,4,6-tribromophenoxy)methyl]-propyl trifluoromethanesulfonate.
[2]The residue % figure represents the weight of the sample remaining at 450° C divided by the original sample weight before exposure to elevated temperatures times 100%. The experimental error in such numbers is approximately ±2%.
[3]All samples exhibited essentially complete weight loss upon continued heating to 650° C.
[4]The additive-containing sample residue at 450° C minus the sample No. 8 residue at 450° C (i.e., 12% ±2%). The experimental error in each of the numbers is approximately ±2%. Thus the resulting error in the calculated difference is approximately ±4%.

The results show that the samples containing triflate esters exhibit significantly more residue at 450° C (i.e., from about 50 percent to about 150 percent more) than the 75:25 styrene/maleic anhydride copolymer control (Sample 8). The data for Sample Nos. 9, 10, 12 and 13 show that equivalent increases in residue at 450° C are not obtained when the corresponding acetate ester is substituted for the triflate ester.

While the present invention has been described with reference to particular embodiments and examples, it should be understood that such embodiments are not intended to limit the scope of the instantly claimed invention.

What is claimed is:
1. A char-forming composition of matter comprising, (A) a polymeric component that comprises (1) polymerized ethylenically unsaturated carboxylic anhydride in an amount sufficient to provide at least about 1 milliequivalent of anhydride moiety per gram of the char-forming composition, and (2) polymerized monovinylidene aromatic monomer in an amount sufficient to provide at least about 1 milliequivalent of reactive aromatic moiety per gram of the char-forming composition, and (B) a char-forming amount of a stable ester of the formula:

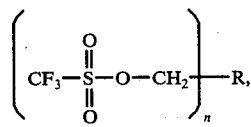

wherein n is a positive integer and R is an n-valent tertiary hydrocarbyl radical or an inertly substituted n-valent tertiary hydrocarbyl radical.

2. A composition of claim 1 wherein the ethylenically unsaturated carboxylic anhydride is an α,β-ethylenically unsaturated carboxylic anhydride.

3. A composition of claim 1 wherein the ethylenically unsaturated carboxylic anhydride is chloromaleic anhydride, bromomaleic anhydride or maleic anhydride.

4. A composition of claim 1 wherein the monovinylidene aromatic monomer is a compound of the formula:

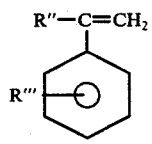

wherein
R" is hydrogen or lower alkyl having from 1 to about 4 carbon atoms and R'" is hydrogen, bromine, chlorine, an alkyl radical of from 1 to about 6 carbon atoms or a haloalkyl radical of from 1 to about 6 carbon atoms which contains from 1 to about 3 atoms of bromine or chlorine.

5. A composition of claim 1 wherein the polymeric component comprises a copolymer containing the ethylenically unsaturated carboxylic anhydride and the monovinylidene aromatic monomer.

6. A composition of claim 1 wherein the stable ester has the formula:

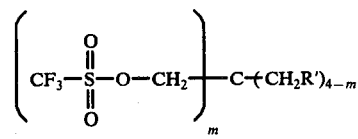

wherein $m$ is 1 or 2 and each R' group is independently bromine or an inertly substituted aliphatic, alicyclic or aromatic halohydrocarbon radical containing from 1 to about 6 carbon atoms and from 1 to about 4 atoms of bromine.

7. A composition of claim 1 wherein the ester is present in an amount sufficient to provide from about 0.1 to about 1 milliequivalent of triflate ester moiety per gram of the char-forming composition.

8. A composition of claim 5 wherein the ethylenically unsaturated carboxylic anhydride is maleic anhydride and the monovinylidene aromatic monomer is styrene.

9. A composition of claim 8 wherein the stable ester has the formula:

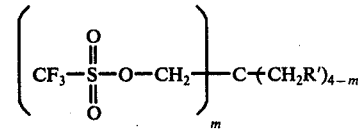

wherein $m$ is 1 or 2 and each R' group is independently bromine or an inertly substituted aliphatic, alicyclic or aromatic halohydrocarbon radical containing from 1 to about 6 carbon atoms and from 1 to about 4 atoms of bromine.

10. A composition of claim 9 wherein (A) the copolymer (1) contains about 25 mole percent maleic anhydride and about 75 mole percent styrene and (2) constitutes from about 85 to about 95 weight percent of the char-forming composition, and (B) the stable ester constitutes from about 5 to about 15 weight percent of the char-forming composition.

* * * * *

UNITED STATES PATENT AND TRADEMARK OFFICE
CERTIFICATE OF CORRECTION

PATENT NO. : 4,038,245
DATED : July 26, 1977
INVENTOR(S) : Charles E. Reineke

It is certified that error appears in the above-identified patent and that said Letters Patent are hereby corrected as shown below:

On the cover sheet, "10 Claims" should read --15 Claims--.

Column 3, line 55, after "reactive" insert --aromatic--;

Column 4, line 23, after "wherein" insert --n--;

Column 4, line 40, delete "atom" and insert --atoms--;

Column 5, line 3, delete "monovalvent" and insert --monovalent--;

Column 6, line 17, delete "the" and insert --The--;

Column 8, Footnote 2, last line, after "1/4" insert --inch--;

Column 9, under the headings, line 2, delete "adjused" and insert --adjusted--;

Column 9, under the headings, line 3, delete the first appearing "the";

Column 9, under the headings, line 4, delete "classificaton" and insert --classification--;

Column 9, under the headings, line 11, delete "aftereach" and insert --after each--;

Column 9, under the headings, lines 13 and 15, delete "specmens" and insert --specimens--;

Column 9, line 26, after "acetate" insert --ester--;

Column 9, line 30, delete "loadins" and insert --loadings--;

UNITED STATES PATENT AND TRADEMARK OFFICE
CERTIFICATE OF CORRECTION

PATENT NO. : 4,038,245
DATED : July 26, 1977
INVENTOR(S) : Charles E. Reineke

It is certified that error appears in the above-identified patent and that said Letters Patent are hereby corrected as shown below:

Column 9, line 36, delete "acetatecon-" and insert
 -- acetate-con- --;

Column 9, line 37, delete "phenomemon" and insert
 --phenomenon--;

Column 10, line 50, "tribromophenoxy)methyl]1,3-propanediol"
 should read --tribromophenoxy)methyl]-1,3-propanediol--;

Column 10, line 56, "2,2-bis[2,4,6-" should read
 -- 2,2-bis[(2,4,6- --;

Column 10, line 58, delete "or" and insert --of--;

Column 10, lines 66 and 67, "2,2-bis[2,4,6-tribromo-phenoxy)
 methyl]-1,3propanediyl" should read --2,2-bis[(2,4,6-tribromo-phenoxy)methyl]-1,3-propanediyl--;

Column 11, line 35, "3,3-bis[2,4,6-tribromophenoxy)methyl-"
 should read -- 3,3-bis[(2,4,6-tribromophenoxy)methyl- --;

Column 11, line 50, delete "trifluoromethanes-" and insert
 -- trifluoromethane- --;

Column 11, line 65, delete "bromomehtyl)-" and insert
 -- bromomethyl)- --;

UNITED STATES PATENT AND TRADEMARK OFFICE
CERTIFICATE OF CORRECTION

PATENT NO. : 4,038,245

DATED : July 26, 1977

INVENTOR(S) : Charles E. Reineke

It is certified that error appears in the above-identified patent and that said Letters Patent are hereby corrected as shown below:

Column 14, line 42, add the following:

--11. The composition of Claim 1 wherein (A) R contains at least one halogen atom selected from the group consisting of bromine and chlorine, and (B) the ratio of halogen atoms to carbon atoms in R is from about 1:10 to about 1:1.

12. The composition of Claim 6 wherein each R' group is independently bromine or tribromophenoxy.

13. The composition of Claim 9 wherein each R' group is independently bromine or tribromophenoxy.

14. The composition of Claim 10 wherein each R' group is independently bromine or tribromophenoxy.

15. The composition of Claim 10 wherein the stable ester is 3-bromo-2,2-bis(bromomethyl)-propyl trifluoromethanesulfonate; 2,2-bis(bromomethyl)-1,3-propanediyl trifluoromethanesulfonate; 3-bromo-2,2-bis[(2,4,6-tribromophenoxy)methyl]-propyl trifluoromethanesulfonate; or 2,2-bis[(2,4,6-tribromophenoxy)methyl]-1,3-propanediyl trifluoromethanesulfonate.--

Signed and Sealed this

Fifteenth Day of November 1977

[SEAL]

Attest:

RUTH C. MASON
Attesting Officer

LUTRELLE F. PARKER
Acting Commissioner of Patents and Trademarks